United States Patent [19]

Nienow

[11] 4,083,253
[45] Apr. 11, 1978

[54] FLUID SAMPLING APPARATUS

[76] Inventor: Harvey Charles Nienow, 918 River La., Santa Ana, Calif. 92706

[21] Appl. No.: 827,951

[22] Filed: Aug. 26, 1977

[51] Int. Cl.² .............................................. G01N 1/12
[52] U.S. Cl. ................................... 73/425.4 R; 294/73
[58] Field of Search ...................... 73/425.4 R; 294/73

[56] References Cited

U.S. PATENT DOCUMENTS

| 3,692,490 | 9/1972 | Hall ................................ | 73/425.4 R |
| 3,826,144 | 7/1974 | Wessels ........................... | 73/425.4 R |

*Primary Examiner*—S. Clement Swisher
*Attorney, Agent, or Firm*—Harvey C. Nienow

[57] ABSTRACT

A fluid sampling apparatus having an elongated member which carries a pivotal platform at one end and a handle at the other end. An operating lever extends from the handle to the platform whereby a vessel attached to the platform can be pivoted by pulling the lever at the handle, thereby moving the vessel from inverted position to upright position to cause fluid at a predetermined depth or level within a body of fluid to enter the vessel.

8 Claims, 6 Drawing Figures

FLUID SAMPLING APPARATUS

The present invention relates generally to fluid sampling apparatuses, and more particularly to such apparatuses for providing a fluid sample from a predetermined depth or level within a body of fluid.

It has been found very desirable, if not necessary, to provide a fluid sample from a large body of fluid to permit of chemical analyses and the like. Not infrequently, such sample must be taken from a particular depth or level within the body of fluid, as for instance when the surface fluid is unrepresentative of the entire body of fluid.

One practical application for taking a fluid sample at a specified depth within a body of fluid, is with respect to swim pools. As is well understood, various chemical characteristics or information of the water in swim pools must be determined periodically so that the most desirable water conditions can be provided. In this regard, the pH of the pool water must be maintained at approximately 6.4 to 6.7 and the total alkalinity must be determined periodically to permit proper steps to be taken such as adding certain chemicals to the water to maintain it in proper condition.

It has been determined that the surface water of a swim pool is not representative of the bulk of the water due to evaporation of water and/or chemicals at or near the surface as well as exposure of the surface water to many different kinds of foreign matter. Thus, it has been determined that any and all chemical tests and analyses of the pool water should be made on a sample which is at least 18 inches below the surface of the pool water.

In view of the foregoing, it is an object of the present invention to provide a fluid sampling apparatus which is operable to provide a sample of fluid at substantially and desired depth within a body of fluid.

Another object of the present invention is to provide a fluid sampling apparatus as characterized above whereby a fluid sample can be obtained below the surface of the fluid without requiring an individual to place or put any part of his body into the body of fluid.

A still further object of the present invention is to provide a fluid sampling apparatus as characterized above whereby substantially any type or size of vessel can be utilized for obtaining the sample.

An even still further object of the present invention is to provide a fluid sampling apparatus as characterized above which is simple and inexpensive to manufacture and which is rugged and dependable in operation.

The novel features which I consider characteristic of my invention are set forth with particularity in the appended claims. The invention itself, however, both as to its organization and mode of operation, together with additional objects and advantages thereof, will best be understood from the following description of specific embodiments when read in connection with the accompanying drawings, in which:

Like reference characters indicate corresponding parts throughout the several views of the drawings.

Figure 1:
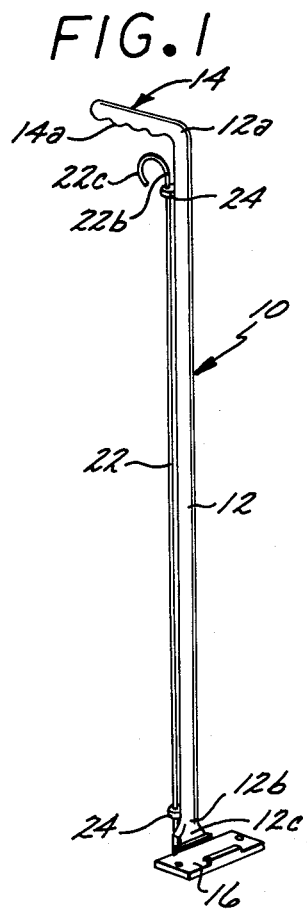
FIG. 1 is a perspective view of fluid sampling apparatus according to the present invention.
Figure 2:
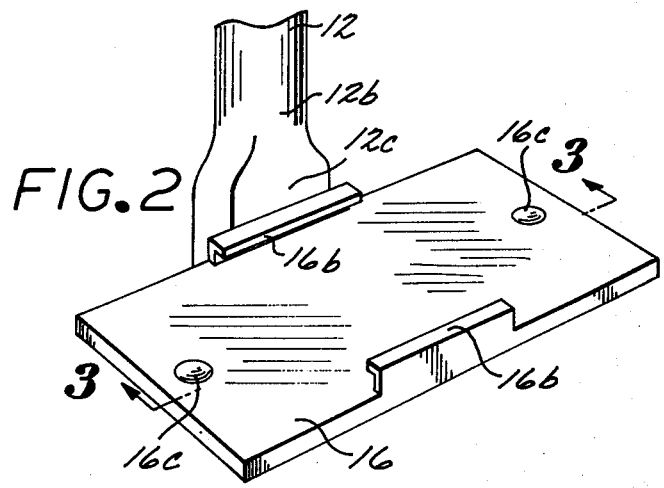
FIG. 2 is a fragmentary perspective view of a portion of the apparatus of FIG. 1.

Referring to FIG. 1 of the drawings, there is shown therein an apparatus 10 for use in obtaining fluid samples at substantially any desired depth within a body of fluid.

It comprises an elongated member 12 which may be cylindrical or tubular in construction, and which is formed with a handle 14 at its upper end portion 12a. Such handle 14 may be provided with finger-grip formations as shown at 14a to facilitate manual gripping of the apparatus 10 as will hereinafter become more apparent.

Figure 6:
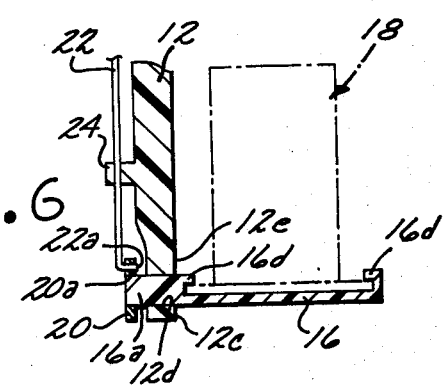
FIG. 6 is a cross-sectional view taken substantially along line 6—6 of FIG. 5 of the drawings.

The lower end portion 12b of member 12 is formed with a generally square or rectangular cross-section as at 12c. As shown most particularly in FIG. 6 of the drawings, end portion 12b is further formed with a through circular opening 12d, the axis of which is substantially at right angles to the length of elongated member 12.

A platform 16 is pivotally mounted on the lower end portion 12b of member 12. Such platform is provided with a tubular or cylindrical extension 16a which fits within the opening 12d. The extension is adapted to rotate or pivot within the opening, relative to member 12.

It may be desirable to provide extension 16a with a flat bearing surface for resting against the surface 12e of the square or rectangular end portion 12c to maintain the platform 16 in proper alignment on the end of member 12.

Platform 16 is provided with any appropriate means, such as the spaced, opposed shoulders or lips 16b, for engaging and retaining a vessel on the platform.

Figure 3:
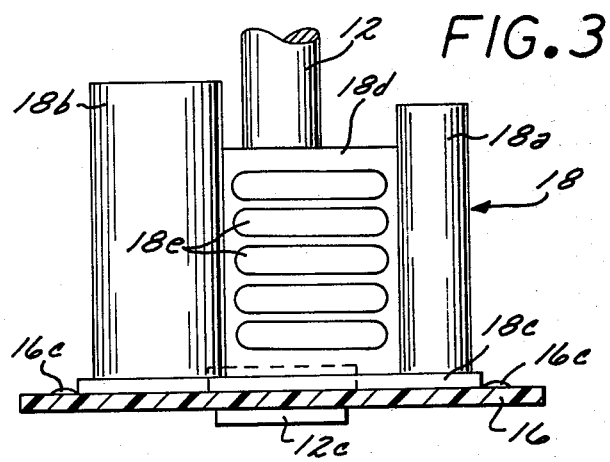
FIG. 3 is a side elevational view, taken substantially along line 3—3 of FIG. 2 of the drawings.
Figure 4:
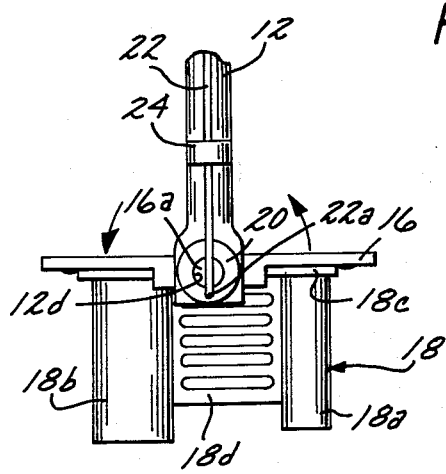
FIG. 4 is a fragmentary side elevational view showing the apparatus in a first position.
Figure 5:
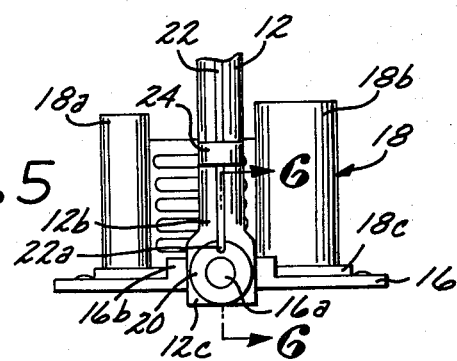
FIG. 5 is a fragmentary side elevational view similar to FIG. 4, showing the apparatus in a second position.

As shown most particularly in FIGS. 3, 4 and 5 of the drawings, substantially any type of vessel may be positioned on platform 16. Shown in these drawings, however, is a sampling device 18 having two vessels 18a and 18b formed integrally with a base 18c. Interconnecting the vessels is a plastic web 18d which carries a color code 18e which is used in making chemical analyses of fluid within the vessels.

The base 18c of device 18 is of such size and shape as to snugly fit between and within the shoulders or lips 16b. It has been found that small protuberances or ribs 16c can be used to retain the sampling device 18 on the platform 16, as shown most particularly in FIG. 3 of the drawings.

Attached to the end of tubular extension 16a is an annular member 20 which acts as a crank arm to convert reciprocal movement to rotary movement as will hereinafter appear. Member 20 is press-fitted onto the end of tubular extension 16a or is firmly attached thereto in any other appropriate manner so as to be integral therewith. Member 20 is further provided with a through opening 20a, offset from the axis of rotation of platform 16 but substantially parallel thereto, to receive the lower end portion of an operating level 22. Such lower end portion 22a is angularly offset and inserted within the opening 20a. An upper end 20b of level 20 is provided with a reversely bent portion 20c which is manually engageable in a trigger fashion as will hereinafter become more apparent.

To retain the lever 20 in substantially parallel relation to elongated member 12 throughout operation of the subject fluid sampling apparatus 10, guide members 24 are provided. Such guide members may be formed integrally with member 12 or may be attached thereto, as desired, and are individually provided with through openings for accomodating the lever 22 to permit of reciprocatable movement thereof relative to member 12.

In operation, the user of the subject sampling apparatus 10, before inserting it into the body of fluid, positions the sampling vessel or vessels in inverted position as shown in FIG. 4 of the drawings. This is accomplished by manually rotating platform extension 16a within opening 12d, thus causing operating lever 22 to be at or near its lowermost position as shown in FIG. 4.

The entire lower end portion of apparatus 10 is then inserted into the body of fluid, the handle 14 being gripped with the individual's index finger in the reversely bent trigger portion 22c of lever 22. The apparatus should be moved vertically downwardly until the vessels to be filled are at the proper or desired depth whereat the fluid sample is to be obtained. When this position is reached, the lever 22 is pulled upwardly by pulling on the reversely bent portion 22c thereof, thereby causing the offset lower end portion 22a to move upwardly relative to the elongated member 12. This causes the platform 16 to be pivoted approximately 180° on the lower end of member 12, to a position wherein the vessels are in an upright position. When this occurs, the air trapped within the vessels 18a and 18b is replaced by fluid at the particular depth of the vessels.

Thereafter, it is a simple matter for the apparatus 10 to be pulled vertically upwardly until the vessels 18a and 18b are free of the body of fluid. The appropriate chemical analyses can then be made with the fluid in the vessels, such fluid having been obtained from the predetermined depth within the body of fluid.

Although I have shown and described certain specific embodiments of my invention, I am well aware that many modifications thereof are possible. My invention is not to be restricted except insofar as is necessitated by the prior art and by the spirit of the appended claims.

I claim:

1. A fluid sampling apparatus for obtaining a fluid sample at a predetermined depth in a body of fluid comprising in combination,
 an elongated member having handle means at one end and being of such length that with said handle means above the surface of a body of fluid the other end may be positioned at a predetermined depth therein,
 a platform adapted to hold a vessel and pivotally mounted on said elongated member at said other end thereof to pivot about an axis at substantially right angles to said elongated member,
 and operating means connected relative to said platform and extending to said handle to pivot said platform and vessel thereon substantially 180°.

2. A fluid sampling apparatus for obtaining a fluid sample at a predetermined depth in a body of fluid according to claim 1,
 wherein said operating means in pivoting said platform said 180° causes said vessel to be moved from inverted to upright position in said fluid.

3. A fluid sampling apparatus for obtaining a fluid sample at a predetermined depth in a body of fluid according to claim 2,
 wherein said operating means is actuatable at said handle means to pivot said platform said 180°.

4. A fluid sampling apparatus for obtaining a fluid sample at a predetermined depth in a body of fluid according to claim 3,
 wherein said elongated member is formed with a transverse opening at said other end and said platform is provided with a tubular extension in said opening and pivotal therein to pivot said platform.

5. A fluid sampling apparatus for obtaining a fluid sample at a predetermined depth in a body of fluid according to claim 4,
 wherein said operating means includes a generally reciprocatable lever extending along said elongated member and having a lower end portion connected to said tubular extension whereby reciprocating movement of said lever effects pivotal movement of said extension and platform.

6. A fluid sampling apparatus for obtaining a fluid sample at a predetermined depth in a body of fluid according to claim 5,
 wherein said lever has an upper end portion adapted to be manually engaged and pulled to effect reciprocating movement of said lever.

7. A fluid sampling apparatus for obtaining a fluid sample at a predetermined depth in a body of fluid according to claim 6,
 wherein said platform is provided with holding means for retaining a vessel having a generally flat base.

8. A fluid sampling apparatus for obtaining a fluid sample at a predetermined depth in a body of fluid according to claim 7,
 wherein said other end of said elongated member is formed with a generally flat surface at right angles to the axis of said opening therein.

* * * * *